United States Patent
Dawson et al.

(10) Patent No.: US 7,048,937 B2
(45) Date of Patent: May 23, 2006

(54) METHODS AND COMPOSITIONS FOR CONTROL OF COCCIDIOSIS

(75) Inventors: Karl A. Dawson, Lexington, KY (US); Arnold E. Sefton, Guelph (CA)

(73) Assignee: Alltech, Inc., Nicholasville, KY (US)

( * ) Notice: Subject to any disclaimer, the term of this patent is extended or adjusted under 35 U.S.C. 154(b) by 153 days.

(21) Appl. No.: 10/206,132

(22) Filed: Jul. 26, 2002

(65) Prior Publication Data

US 2003/0091589 A1    May 15, 2003

Related U.S. Application Data

(60) Provisional application No. 60/308,215, filed on Jul. 27, 2001.

(51) Int. Cl.
*A01N 25/32* (2006.01)
(52) U.S. Cl. .................. 424/406; 424/93.51; 424/438; 424/442; 426/62; 514/54
(58) Field of Classification Search ................ 424/405, 424/406, 438, 442, 93.51; 514/26, 27, 54; 426/9, 53, 62
See application file for complete search history.

(56) References Cited

U.S. PATENT DOCUMENTS

| | | | |
|---|---|---|---|
| 5,063,219 A | 11/1991 | Schildknecht et al. | 514/157 |
| 5,703,060 A | 12/1997 | McAnalley et al. | 514/54 |
| 6,045,834 A | 4/2000 | Howes et al. | 426/2 |

FOREIGN PATENT DOCUMENTS

| | | |
|---|---|---|
| EP | 0 965 346 A2 | 12/1999 |
| EP | 1 082 909 A1 | 3/2001 |

OTHER PUBLICATIONS

OLSEN mannanoligosaccharides—Proceedings of Alltech's 11th Annual Symposium, May 8-10, pp 389-392, 1995.*
*Alltech* (printed Feb. 7, 2001) Announcement <http://www.alltech-bio.com/alltech%5CAlltech/News_The_list_of_positive_results_gets_longer>.
*Chisolm Trail Loft* (printed Jul. 15, 2002) Advertisement, <http://www.redroselofts.com/what_we_use.htm>.
*Chisholm Trail Loft* (printed Jul. 15, 2002) Advertisement, <http://www.ctlloft.com/how_ctl_products_work.html>.

* cited by examiner

*Primary Examiner*—Neil S. Levy
(74) *Attorney, Agent, or Firm*—King & Schickli, PLLC

(57) ABSTRACT

Feeding yeast cell wall-containing compositions, including those compositions comprising mannanoligosaccharide(s), to animals exposed to or infected with coccidia, especially poultry exposed to pathogenic species of *Eimeria*, results in improved livestock performance and physical condition as compared with those animals who were not fed such compositions.

14 Claims, No Drawings

METHODS AND COMPOSITIONS FOR CONTROL OF COCCIDIOSIS

CROSS REFERENCE TO RELATED APPLICATIONS

This application claims benefit of U.S. Provisional Application No. 60/308,215, filed Jul. 27, 2001.

ACKNOWLEDGMENT OF FEDERAL RESEARCH SUPPORT not applicable.

BACKGROUND OF THE INVENTION

This invention relates to methods and compositions for the control of coccidial infections in animals. In particular, the invention relates to the use of yeast cell and yeast cell wall-containing preparations for use in control of coccidial infections in mammalian and avian species.

Coccidiosis is a protozoan parasitic infection of mammals and birds caused by species of the coccidia *Eimeria* resulting in intestinal lesions, diarrhea, enteritis and death. *Eimeria* spp. (*E. tenella, E. maxima,* and *E. acervulina*) are three of the most common coccidia that plague the poultry industry. These species differ in their mode of action. *E. tenella* attacks the cecum, whereas *E. maxima* and *E. acervulina* attack the mid and upper regions of the intestinal tract, respectively.

Coccidiosis is an economically important disease in domestic livestock production and even in less severe infections, losses in feed conversion efficiency and decreased weight gains may represent the difference between profit and loss in modem, intensive animal production situations. Coccidial infections are known to be a predisposing factor to other syndromes, in particular, necrotic enteritis (a bacterial infection of the intestinal lining resulting in necrosis of the intestinal lining in various regions of the gut).

Coccidial organisms survive in the environment because of their exceptional reproductive ability and because of the composition of the walls of their oocysts, which provides extraordinary survival abilities for significant periods of time. Oocysts are disseminated via the feces and litter but may also be disseminated in an airborne fashion, such as by movement of dust, and by vector organisms such as earthworms, beetles, flies, and other pests. Because it is standard practice in the poultry industry, for example, to reuse litter, coccidia in litter from previous infected flocks serves as a reservoir for future infections.

Conventional disinfectants are relatively ineffective against coccidia. Thorough cleaning of housing and strict bio-security measures are necessary to maintain proper hygiene and reduce the number of oocysts to which animals and birds are exposed. Unfortunately, due to relatively rapid turnaround of potential host animals (for example, the rapid replacement of flocks in broiler operations), a permanent reservoir of oocysts is often maintained. Even a few oocysts are capable of initiating a massive infection in a few weeks. Accordingly, control measures that go beyond maintenance of proper hygiene are required.

Currently known methods of coccidial control include use of anticoccidial medication and vaccination protocols. Anticoccidial drugs are generally effective for their intended purpose; they advantageously are provided in the feed or via the drinking water to animals being treated. Exemplary drugs include ionophores (Monensin, lasalocid) and chemical anticoccidials. A significant disadvantage of current drugs used for treatment/control of coccidia is that, over time, treated organisms may become resistant to particular drugs. Accordingly, different drugs must be used, often in rotation or in a staggered schedule (shuttle programs), to prevent development of resistant organisms. Even in cases where shuttle programs are implemented, it is possible that efficacy against coccidial infections will be compromised during the period when anticoccidial drugs are altered. Additionally, certain drugs, while useful in the control of coccidiosis, require a predetermined withdrawal period prior to slaughter or consumption of animal products to address safety issues associated with the sale of meat, milk and eggs from treated animals.

Currently employed vaccines against coccidial organisms are also generally effective for their intended purpose, creating an active immunity against infection in treated animals. Vaccines are costly and suffer from the disadvantage that they must contain the appropriate antigens to stimulate a protective immune response to each species of coccidial organism involved in disease processes. In poultry, for example, this could be any or all of the seven species of the genus Eimeria that infect chickens. Further, vaccination protocols may cause subclinical infections of varying severity, and thus, negatively affect performance in those vaccinated animals.

Accordingly, there remains a need in the art for alternative methods for controlling coccidial infections in livestock, with the benefit of improved productivity and economics and where those alternate methods do not lead to the development of resistant organisms and/or require long withdrawal periods prior to slaughter.

SUMMARY OF THE INVENTION

The present invention provides methods and compositions for preventing, reducing or ameliorating coccidial infections in livestock, including swine and poultry. The compositions may be generally described as yeast cell or yeast cell wall-containing preparations. In one embodiment, the compositions of the present invention comprise preparations derived from yeast cell walls, where those preparations comprise significant amounts of mannanoligosaccharide(s), for example, mannanoligosaccharides. The method of the present invention comprises feeding an amount of a yeast cell wall-containing or yeast cell-containing composition to an animal effective for preventing or reducing coccidial infections, or for ameliorating the harmful effects of a coccidial infection, once established, in the animal to which the composition is fed. The mannanoligosaccharide and/or yeast cell wall-containing or yeast cell-containing composition can be incorporated into the animal's feed rations or the composition can be provided as a supplement fed to the animal. Those compositions of the present invention can be prepared from an edible yeast including, but not limited to, *Saccharomyces cerevisiae* (or other *Saccharomyces* species), *Candida, Kluyveromyces* or *Torulaspora.* As specifically exemplified herein, the yeast-derived preparation is prepared from cells of *Saccharomyces cerevisiae* NCYC 1026. Further improvement in the prevention, reduction or amelioration of coccidial infections can be achieved when the yeast cell- or yeast cell wall-containing compositions further contain an anti-coccidial ionophore (e.g., monensin or lasalocid) and/or a steroidal surfactant (such as sapogenin).

Still other objects of the present invention will become apparent to those skilled in this art from the following description wherein there is shown and described a preferred embodiment of this invention, simply by way of illustration of one of the modes best suited to carry out the invention. As it will be realized, this invention is capable of other different embodiments and its several details are capable of modification in various, obvious aspects all without departing from the invention. Accordingly, the descriptions herein will be regarded as illustrative in nature and not as restrictive.

DETAILED DESCRIPTION OF THE INVENTION

The present invention provides a novel method for preventing, reducing or ameliorating coccidial infections in animals. In particular, the invention provides a method for preventing or ameliorating coccidial infections in animals comprising feeding an effective amount of a yeast derived preparation, desirably containing yeast cell wall materials including mannanoligosaccharides. The yeast cell-derived preparations for use in the compositions and methods of the present invention can be made using cells of any of a number of edible yeasts including, but not limited to, *Saccharomyces, Candida, Kluyveromyces,* or *Torulaspora* species. In a specifically exemplified embodiment, the yeast is *Saccharomyces cerevisiae* strain NCYC 1026. This strain is on deposit with the American Type Culture Collection, Manassas, Va. (Accession No. 46785) and with the Agricultural Research Service, Peoria, Ill. (Accession No. NRRL Y-11875). As specifically exemplified, the yeast cell-derived composition is commercially available from Alltech, Inc., Nicholasville, Ky. (BIO-MOS®). This composition contains yeast cell wall material and yeast-derived mannanoligosaccharide.

The compositions of this invention as described herein can be fed as supplements or incorporated into commercially available feeds. One of ordinary skill in the art recognizes that the amounts of the composition fed varies depending upon the animal species, the age of the animal, the size of the animal, and the type of feedstuff to which the composition is added or according to usage as a separate nutritional supplement.

The methods of the instant invention, and the compositions described therewith, are suitable for preventing or ameliorating coccidial infections in any animal, including, but not limited to, bovine, porcine, avian, equine, ovine, lapine, and caprine species. Not all herds or flocks are infected with coccidia nor are all agricultural environments. Avians to which the yeast cell wall-containing compositions can be fed to prevent, reduce or ameliorate coccidial infections include poultry, pigeons, and companion birds (macaws, parakeets, cockatoos, canaries, finches, parrots and the like). Birds raised for egg production, meat or sport include, without limitation, quail, grouse, pheasants, chickens, geese, ducks, turkeys, and others. Mammals can also benefit from the yeast-derived supplementation, especially those agriculturally important animals, such as swine, cattle, bison, horses, sheep, goats and so on.

Clinical challenge studies consist of infecting young birds orally with a specific dose of coccidia, and then measuring the level of infection, the damage to the intestinal tissue, mortality, and the negative effects of infection on performance (weight gain and feed conversion).

Feeding birds a yeast cell-derived composition, especially a yeast cell wall and mannanoligosaccharide-containing composition prepared as described herein below, reduced the rate of injury, and the negative effects from infection on weight gain and severity of intestinal lesions, as illustrated in the Examples below. These Examples are not to be construed as imposing any limitation on the scope of the present invention. Further improvement in performance with respect to anti-coccidial effects can be obtained when the yeast cell-containing or yeast cell wall-containing compositions also contain an anticoccidial ionophore such as monensin or lasalocid and/or an anticoccidial steroidal sapogenin (see, e.g., EP 1,082,909).

Abbreviations and nomenclature, where employed, are deemed standard in the field and commonly used in professional journals such as those cited herein.

All references cited in the present application are incorporated by reference herein to the extent that there is no inconsistency with the present disclosure.

EXAMPLES

Example 1

A 28-day trial with 360 Cornish Rock male broiler chicks was conducted to investigate the effects of two medicated feeds on the suppression of detrimental effects of *E. tenella* (See Tables I & II).

Day-old chicks were fed standard corn soya diets containing Monensin (60 g/kg) or a yeast cell wall/mannanoligosaccharide-containing composition (BIO-MOS®, Alltech, Inc., Nicholasville, Ky.) (1 kg/tonne). The experimental groups included: 1) negative control (unmedicated, unchallenged); 2) positive control (untreated, challenged); 3) Monensin-treated, challenged and 4) BIO-MOS®-treated, challenged. Birds were randomly assigned to three replicate pens in each treatment group. At 14 days of age, chicks were infected orally by gavage with *E. tenella* (50,000 oocysts/bird). The response variables measured included weekly body weight gain and cecal lesion scores as described (Johnson and Reid. 1970 "Anticoccidial Drugs: Lesion Scoring Technique in Battery and Floor Pen Experiments with Chickens." *Exp. Parasitol.* 28:30–36). Treatment differences were evaluated by using the LSD procedure with the General Linear Models Procedure (SAS Institute, 1985, Cary, N.C.) using pens as the experimental units. The model statement included only treatment effects. When significance differences (P<0.05) were observed, the least significant differences (LSD) procedures was applied to test for the differences among treatments.

Administration of both Monensin and BIO-MOS® significantly (P<0.05) reduced the severity of the *E. tenella* infections as measured by cecal lesion scores (Table I). The improved health status of the birds receiving BIO-MOS® was reflected in improvements in the mean weight gains relative to the *E. tenella*-challenged control (Table II). The mean weight gain of birds receiving BIO-MOS® was similar to that observed in the unchallenged (healthy) control group and 5% greater than that observed in the untreated *E. tenella*-challenged group. Similar improvements in weight gain were not seen in birds receiving the standard Monensin treatment.

Example 2

A 28-day trial with 360 Cornish Rock male broiler chicks was conducted to investigate the effects of two medicated feeds on the suppression of *E. maxima* infection. Thirty day-old chicks per treatment group were housed in battery cages and fed a standard soya corn diet containing Monensin (60 g/kg) or a commercially available yeast cell-derived composition containing yeast cell wall material and mannanoligosaccharide (BIO-MOS®) (1 kg/tonne). The four experimental groups included: 1) negative control (unmedicated, unchallenged); 2) positive control (unmedicated, challenged); 3) Monensin treated, challenged, and 4) BIO-MOS® treated, challenged. Birds were assigned to treatments and replicate pens as described in Example 1.

At 14 days of age, chicks were infected orally by gavage with *E. maxima* (50,000 oocysts/bird). The response variables measured included weekly body weight gain and cecal lesion scores. Such measurements were subjected to analysis of variance as described in Example 1.

Monensin and BIO-MOS® treatments each significantly reduced cecal lesion scores associated with *E. maxima* infections. Monensin reduced average cecal lesion scores by 21% and BIO-MOS® reduced average cecal lesion scores by 28% (Table III). These results confirm that BIO-MOS® dietary supplementation ameliorates the severity of cecal lesions caused by *E. maxima* infection.

Average body weight gain of BIO-MOS®-treated chicks for weeks 2–4 was 27% of the average body weight gain of the positive control (untreated, challenged) chicks (Table IV) and was more effective than monensin in overcoming the depressed growth associated with coccidial challenge. Accordingly, chicks fed BIO-MOS® were able to maintain body weight gain as a measure of performance in the presence of *E. maxima* challenge.

Example 3

A 28-day trial with 360 Cornish Rock male broiler chicks was conducted to investigate the effects of two medicated feeds on the suppression of detrimental effects of *E. acervulina*.

Day-old chicks were fed a standard corn soya diet containing Salinomycin (6 mg/kg) or BIO-MOS® (1 kg/tonne). The four experimental groups were: 1) negative control, unmedicated, unchallenged; 2) Salinomycin-treated, challenged, 3) BIO-MOS®-treated, challenged and 4)BIO-MOS® treated, unchallenged. Birds were randomly assigned to three replicate pens in each treatment group. At 14 days of age, chicks were infected orally by gavage with *E. acervulina* (500,000 oocysts/bird). The response variables measured included weekly body weight gain and cecal lesion scores. Data were subjected to ANOVA using the General Linear Model procedure (SAS Institute, Cary, N.C.) as described in Example 1.

BIO-MOS®, like salinomycin, significantly reduced severity of cecal lesions as measured by cecal lesion scores. BIO-MOS® reduced severity of lesions by 49% and salinomycin by 57% (Table V). BIO-MOS®-treated chicks had an average mean body weight gain of 12% over the positive control (Table VI). The results confirm that the addition of the yeast cell wall preparation can be used to maintain the performance of chicks challenged with *E. acervulina*.

Example 4

A 20-day battery trial was conducted to determine the anticoccidial activity of a yeast cell composition in broiler chicks (Cobb) challenged with sporulated *Eimeria* species. One hundred sixty chicks (day old) were housed in battery cages (10 chicks per cage, 459 sq. cm/bird). There were four replicated cages per treatment. A standard corn soya diet was provided with water ad libitum. Treatment groups were the following: (1) Negative control (non-medicated, unchallenged); 2) positive control (non-medicated, challenged); 3) BIO-MOS®, 1 kg/tonne (challenged); and 4) Salinomycin, 60 g/tonne (challenged).

The challenge inoculum was provided at 14 days of age and contained 50,000 *E. acervulina*, 5,000 *E. maxima* or 40,000 *E. tenella* oocysts, respectively, administered by oral gavage. Body weights and feed consumption were measured at 9, 14 and 20 days of age. Six days post-infection all birds were sacrificed and lesion scored using the method of Johnson and Reid (1970) supra. Lesion scores were evaluated in the upper (*E. acervulina*), middle (*E. maxima*), and cecal (*E. tenella*) regions of the intestine.

Cecal lesion scores for the BIO-MOS®-treated and salinomycin-treated chicks were each significantly reduced ($P<0.05$) as compared to both control groups in the upper and mid intestine regions (Table VII). Cecal lesion score reduction for the two treated groups indicate that both BIO-MOS® and salinomycin imparted control of the coccidial challenge as compared to the untreated, challenged control.

Post-challenge weight gains were significantly lower ($P<0.05$) in the challenged control (18.48%) than in the unchallenged control (Table VIII). A less severe reduction in weight (11.6%) was observed in chicks receiving BIO-MOS®.

BIO-MOS® reduced lesion scores and improved post-challenge weight gain when challenged with *Eimeria*. These findings support the conclusion that BIO-MOS® reduces severity of infection and enhances performance in the presence of coccidial infection.

Example 5

A 20-day battery trial was conducted to determine the anticoccidial activity of a BIO-MOS® in broiler chicks (Cobb) challenged with sporulated *Eimeria* species. One hundred sixty chicks (day old) were housed in battery cages (10 chicks per cage, 459 sq. cm/bird). There were 4 replicated cages per treatment. A standard soya corn diet was provided with water ad libitum. Treatment groups were the following: 1) Negative control (non-medicated, unchallenged); 2) Positive control (non-medicated and challenged; 3) BIO-MOS®, 1 kg/tonne (challenged); and 4) Salinomycin, 60 g/tonne (challenged).

The challenge inoculum was provided at 14 days of age and contained respectively, 50,000 *E. acervulina*, 5,000 *E. maxima* or 40,000 *E. tenella* oocysts administered by oral gavage. Body weights and feed consumption were measured at 0, 14 and 20 days of age.

Six days post infection all birds were sacrificed and lesion scored, using the method of Johnson and Reid supra. Lesion scores were evaluated in the upper (*E. acervulina*), middle (*E. maxima*), and cecal (*E. tenella*) regions of the intestine.

BIO-MOS®-treated and salinomycin-treated groups had significantly lower lesion scores than the positive control in all regions of the gut (Table IX). BIO-MOS® reduced lesion scores by 33%. BIO-MOS® was also useful in maintaining the performance of the birds as reflected in a 104% post-challenge weight gain compared to the positive control (untreated, challenged) (Table X). This post-challenge increase in weight gain reflects improved performance in the presence of an *Eimeria* infection.

Example 6

Three 42-day trials were conducted to evaluate the effects of AVATEC (lasalocid, Alpharma, Fort Lee, N.J.), an anticoccidial ionophore (90.7 g/ton); Bacitracin Zn, (50 g/t), and BIO-MOS® (0.5 kg/tonne) on the growth of broiler chicks reared on recycled litter. Sixty (day-old) Cornish Rock male broiler chicks were put into each of four treatment groups (replicated three times) consisting of the following: 1) Control (untreated birds); 2) BIO-MOS® treated, 3) AVATEC treated, and 4) Bacitracin ZN treated. Pine wood shavings on which broilers infected with *E. tenella, E. maxima,* and *E. acervulina* had been grown were used as recycled litter for the trials. Pens containing this recycled litter were assigned to the four treatment groups prior to commencement of the trial, and day old chicks were introduced for each of the three subsequent trials with the same recycled litter.

Diets consisted of mainly corn-soy supplemented with necessary vitamins and minerals to satisfy 1994 National Research Council requirements. Weekly body weights were measured. Mean body weights of chicks fed diets supplemented with BIO-MOS® were significantly greater than controls (P<0.05) and were comparable to those of chicks fed Bacitracin and AVATEC (lasalocid) in all three trials (Table XI). Mean body weight averages of chicks in all treatments decreased with each cycle of litter re-use due to infection. However, the mean body weights of chicks receiving BIO-MOS® for each of the three trials averaged 7% higher than the average body weights of the control group, demonstrating the ability of BIO-MOS® to maintain performance in the presence of a coccidial challenge.

Example 7

Two hundred (one day-old) chicks were housed in ten microbial isolation chambers. At 15 days of age, 150 were randomly allocated, equally in 10 microbial isolation chambers. Chicks in the five control chambers received untreated broiler starter ration; those in the treatment chambers received the same ration to which 0.1% BIO-MOS® was added. On day 22 all chicks received $2.9 \times 10^5$ *E. acervulina* oocysts by oral gavage. Feces were collected under raised wire mesh floors daily in each chamber, and oocysts were counted from days 21–35. Fecal oocyst counts of treated chicks were lower (P<0.05) on days 26, 27, and 29, demonstrating that BIO-MOS® significantly reduced oocysts at peak infection. This reflects the ability of BIO-MOS to reduce proliferation of *E. acervulina* in a poultry production system.

Example 8

In the experiments described herein, yeast-derived compositions are prepared using cells of *S. cerevisiae* strain NCYC 1026 (American Type Culture Collection, Manassas, Va., Accession No. 46885; Agricultural Research Service, Peoria, Ill., NRRL Accession No. Y-11875). The yeast cell wall extract is obtained by methods commonly known in the art. (See, Peppler, H. J. 1979. Production of Yeasts and Yeast Products. Page 157 in: *Microbial Technology & Microbial Processes,* Vol. 1 ($2^{nd}$ Ed.), Academic Press). Briefly, the yeast organism is grown following common techniques used in food-related fermentations and in the beverage industry. Complex media allowing for rapid proliferation of the yeast cells are used. Any of a number of common sugar-containing media, such as diluted molasses, can be used for cell growth. Other medium components may be employed including corn, wood sugars, sulfite waste liquor, and whey. The yeast cells are then separated from the spent medium by centrifugation, for example, washed and again collected to yield a "yeast cream".

Following separation, the cells in the yeast cream are lysed. Any of a number of methods common in the art may be utilized to lyse the yeast organisms, including autolysis, hydrolysis or mechanical means (freeze-thaw, extrusion or sonication). As specifically exemplified, the yeast cell suspension is diluted with water to a concentration of 10–12% dry solids and then heated to a temperature of 140° F. Th pH is adjusted to approximately 8.5, for example with sodium hydroxide. A protease such as papain or any of a number of alkaline or neutral proteases can be added during the lysis phase to accelerate the solubilization of yeast proteins in the disrupted cell material. After an initial incubation with a protease, generally about 2 hours, the pH is adjusted to about 8.0 and the temperature of the mixture is slowly increased to approximately 158° F. The mixture is held at about 158° F. for about 30 min. The resulting yeast cell wall-containing particulate material is collected by centrifugation to remove low molecular weight intracellular components and concentrate the cell wall extract. The resulting concentrate is dried (by any of a number of methods common in the art, including spray-drying or drum drying) to form a hygroscopic, water-soluble powder. The dried powder can be added directly to animal feed rations at rates from about 0.5 to about 20 kg/tonne, and all values and ranges therebetween.

The foregoing examples demonstrate that the methods of the present invention, i.e., providing a yeast cell-derived composition to animals at risk of contracting coccidial infections, are effective in reducing ill effects of coccidial infections. The present invention was effective at reducing harmful effects of coccidial infection by commonly encountered coccidial organisms, and under conditions representative of modern livestock production. Further, the methods and compositions of the instant invention were comparable or superior to existing methods of control of coccidial infection including treatments with Monensin and salinomycin. Advantageously, the methods and compositions of this invention allow amelioration of harmful effects of coccidial infection without risk of creating resistant coccidial organisms, and without requiring an extended pre-slaughter withdrawal period prior to sale of eggs, meat or milk from treated animals.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

TABLE I

Effects of Monensin and BIO-MOS ®
Treatments on Cecal Lesion Scores of Chicks
Infected with *E. tenella.*

| Treatments | Cecal Lesion Scores |
|---|---|
| Negative Control | 0.83[b] |
| Positive Control | 3.17[a] |
| Monensin | 1.50[b] |
| BIO-MOS ® | 1.33[b] |

[a-b]Means within columns with different superscripts are statistically different (p < .05

TABLE II

Effects of Monensin and BIO-MOS ® Treatments on Average Weight Gain in Grams of Chicks Infected with *E. tenella* During Weeks 2–4 After Challenge

| Treatments | 1 | 2 | 3 | Mean | SD |
|---|---|---|---|---|---|
| Negative Control | 730 | 498 | 589 | 606 | 164.4 |
| Positive Control | 585 | 543 | 606 | 578 | 100.5 |
| Monensin | 498 | 611 | 523 | 544 | 312.5 |
| BIO-MOS ® | 595 | 655 | 564 | 605 | 85.3 |

TABLE III

Effects of Monensin and BIO-MOS ® Treatments on Cecal Lesion Scores of Chicks Challenged with *E. maxima*

| Treatments | Cecal Lesion Scores |
|---|---|
| Control | $0.85^b$ |
| Positive Control | $2.33^a$ |
| Monensin | $0.93^b$ |
| BIO-MOS ® | $1.67^b$ |

$^{a-b}$Means within columns with different superscripts are statistically different (p < .05)

TABLE IV

Effects of Monensin and BIO-MOS ® Treatments on Average Weight Gain of Chicks Infected with *E. maxima* 2–4 Weeks After Challenge

| Treatments | 1 | 2 | 3 | Mean | SD |
|---|---|---|---|---|---|
| Negative Control | 730 | 498 | 589 | 606 | 164.7 |
| Positive Control | 385 | 443 | 505 | 444 | 112.82 |
| Monensin | 598 | 412 | 599 | 536 | 142.9 |
| BIO-MOS ® | 613 | 541 | 582 | 565 | 83.1 |

TABLE V

Effects of Salinomycin and BIO-MOS ® on Cecal Lesion Scores of Chicks Challenged with *E. acervulina*

| Treatments | Cecal Lesion Scores |
|---|---|
| Control | $0.81^c$ |
| Positive Control | $2.14^b$ |

TABLE V-continued

Effects of Salinomycin and BIO-MOS ® on Cecal Lesion Scores of Chicks Challenged with *E. acervulina*

| Treatments | Cecal Lesion Scores |
|---|---|
| BIO-MOS ® | $1.101^a$ |
| Salinomycin | $0.92^{bc}$ |

$^{a-b}$Means within columns with different superscripts are statistically different (p < .05)

TABLE VI

Effects of Salinomycin and BIO-MOS ® Treatments on Body Weight Gain of Chicks at 2, 3, 4 Weeks Pre and Post Challenge with *E. acervulina*

| Treatments | Challenge | Body Weight Pre-Infection (grams) Week 2 | Body Weight Gain Post-Infection (grams) Week 3 | Week 4 |
|---|---|---|---|---|
| Control | No | $194^b$ | $351^{ab}$ | $580^{ab}$ |
| Control | Yes | $195^b$ | $293^b$ | $533^b$ |
| Salinomycin | Yes | $236^a$ | $350^a$ | $607^{ab}$ |
| BIO-MOS ® | No | $234^a$ | $370^a$ | $659^a$ |
| BIO-MOS ® | Yes | $232^a$ | $332^{ab}$ | $599^{ab}$ |

$^{a-b}$Means within columns with different superscripts are statistically different (p < .05)

TABLE VII

Effects of Salinomycin and BIO-MOS ® Treatments on Average Cecal Lesion Scores in Chicks Infected with *Eimeria spp.*

| Treatment | Upper | Mid | Ceca | Total |
|---|---|---|---|---|
| Negative Control | 0.0 | 0.0 | 0.0 | 0.0 |
| Positive Control | 2.3 | $1.8^a$ | $2.7^a$ | $6.7^a$ |
| BioMos 1 kg/t | $1.7^b$ | $1.3^b$ | $1.5^b$ | $4.5^b$ |
| Salinomycin 60 g/t | $1.3^c$ | $0.8^c$ | $0.6^c$ | $2.7^c$ |

TABLE VIII

Effects of Salinomycin and BIO-MOS ® Treatments on Feed Conversion, Average Weight Gain and % Reduction in Weight of Chicks Infected with *Eimeria spp.*

| Treatment | Feed Conv. | Avg. Live Wt. Gain (kg) Day 0–14 | Day 0–20 | Day 14–20 | % Wt. Gain Reduction |
|---|---|---|---|---|---|
| Negative Control | $1.431^b$ | $0.640^a$ | $0.640^a$ | $0.312^a$ | 0.00 |
| Positive Control | $1.555^a$ | $0.592^b$ | $0.592^b$ | $0.255^b$ | 18.48 |
| BIO-MOS 1 kg/t | $1.538^a$ | $0.617^{ab}$ | $0.617^{ab}$ | $0.276^b$ | 11.59 |
| Salinomycin 60 g/t | $1.511^b$ | $0.634^a$ | $0.634^a$ | $0.314^a$ | −0.41 |

$^{a-b}$Means within columns with different superscripts are statistically different (p < .05)

TABLE IX

Effects of BIO-MOS ® and Salinomycin Treatments on Average Cecal Lesion Scores of Chicks Infected with Eimeria spp. in Upper, Mid, and Cecal Regions of Intestines

| Treatment | Upper | Mid | Ceca | Total |
|---|---|---|---|---|
| Negative Control | $0.0^c$ | $0.0^b$ | $0.0^d$ | $0.0^d$ |
| Positive Control | $1.6^a$ | $1.6^a$ | $2.5^a$ | $5.8^a$ |
| BioMos 1 kg/t | $0.9^b$ | $1.1^b$ | $1.9^{ab}$ | $3.9^{ab}$ |
| Salinomycin 60 g/t | $0.8^b$ | $0.7^b$ | $1.2^b$ | $2.7^{ab}$ |

TABLE X

Effects of BIO-MOS ® and Salinomycin Treatments on Feed Conversion, Average Live Weight Gain and % Weight Reduction of Chicks Infected with Eimeria spp.

| Treatment | Feed Conv. | Avg. Live Wt. Gain (kg) | | | % Wt. Gain Reduction |
| | | Day 0–14 | Day 0–20 | Day 14–20 | |
|---|---|---|---|---|---|
| Negative Control | $1.575^b$ | $0.257^a$ | $0.523^a$ | $0.266^a$ | 0.00 |
| Positive Control | $1.826^a$ | $0.248^a$ | $0.473^b$ | $0.226^b$ | 15.24 |
| BIO-MOS 1 kg/t | $1.787^a$ | $0.281^a$ | $0.516^a$ | $0.235^{ab}$ | 11.59 |
| Salinomycin 60 g/t | $1.675^a$ | $0.262^a$ | $0.504^{ab}$ | $0.243^{ab}$ | 8.90 |

$^{a-b}$Means within columns with different superscripts are statistically different ($p < .05$)

TABLE XI

Effects of AVATEC, Bacitracin ZN and BIO-MOS ® Treatments on Body Weights of Chicks Grown on Eimeria spp. Infected Recycled Litter

| Treatment | Body Weight in Grams | | |
| | Trial 1 | Trial 2 | Trial 3 |
|---|---|---|---|
| Control | $1993^b$ | $1696^c$ | $1696^b$ |
| AVATEC2 | $2271^a$ | $1863^b$ | $1760^{ab}$ |
| Bacitracin Zn3 | $2272^a$ | $2211^a$ | $1819^a$ |
| BIO-MOS ® | $2186^a$ | $1832^b$ | $1760^{ab}$ |

$^{a-b}$Means within columns with different superscripts are statistically different ($p < .05$)

What is claimed is:

1. A method for reducing coccidial infection in an animal suffering from or exposed to coccidial infection, said method comprising the step of feeding to said animal an amount of a composition comprising yeast cell walls and at least one yeast-derived mannanoligosacoharide effective for reducing coccidial infection;
    wherein the method further includes the step of monitoring the animal for the presence of coccidial infection or for cecal lesions before or after the step of feeding said composition.

2. The method of claim 1, whereby said composition is admixed with a feed ration prior to feeding to said animal.

3. The method of claim 1, whereby said composition is fed to an animal as a dietary supplement.

4. The method of claim 2, wherein the composition comprising yeast cell walls is fed to the animal in an amount providing from about 0.5 to about 20 kg of yeast cell wall per tonne of feed.

5. The method of claim 1, wherein said mannanoligosaccharide-containing composition is formulated for feeding to bovine, porcine, avian, equine, ovine, lapine, and caprine species.

6. The method of claim 1 wherein said composition is derived from a species selected from the group consisting of *Saccharomyces, Candida, Kluyveromyces* and *Torulaspora*.

7. The method of claim 6 wherein said composition is derived from *Saccharomyces cerevisiae*.

8. The method of claim 7 wherein the composition is derived from *Saccharomyces cerevisiae* strain NCYC 1025.

9. The method of claim 1 wherein the composition comprises dried cells of yeast.

10. The method of claim 1 wherein the composition further comprises mannanoligosaccharide.

11. The method of claim 5 wherein the animal is a porcine or an avian species.

12. The method of claim 11 wherein the avian species is a chicken, turkey, duck, goose, pheasant, quail or a companion bird.

13. The method of claim 1 wherein the composition further comprises at least one anticoccidial ionophore.

14. The method of claim 1 wherein the composition further comprises at least one anticoccidial steroidal sapogenin.

* * * * *

UNITED STATES PATENT AND TRADEMARK OFFICE
CERTIFICATE OF CORRECTION

PATENT NO.        : 7,048,937 B2
APPLICATION NO.   : 10/206132
DATED             : May 23, 2006
INVENTOR(S)       : Dawson et al.

It is certified that error appears in the above-identified patent and that said Letters Patent is hereby corrected as shown below:

Claim 8, line 49, please replace "1025" with -- 1026 --.

Signed and Sealed this

Fifteenth Day of August, 2006

JON W. DUDAS
*Director of the United States Patent and Trademark Office*